United States Patent
Moore et al.

(10) Patent No.: US 6,926,672 B2
(45) Date of Patent: Aug. 9, 2005

(54) ELECTRET ACOUSTIC TRANSDUCER ARRAY FOR COMPUTERIZED ULTRASOUND RISK EVALUATION SYSTEM

(75) Inventors: Thomas L. Moore, Livermore, CA (US); Karl A. Fisher, Brentwood, CA (US)

(73) Assignee: Barbara Ann Karmanos Cancer Institute, Detroit, MI (US)

( * ) Notice: Subject to any disclaimer, the term of this patent is extended or adjusted under 35 U.S.C. 154(b) by 115 days.

(21) Appl. No.: 10/323,718

(22) Filed: Dec. 18, 2002

(65) Prior Publication Data

US 2004/0122322 A1 Jun. 24, 2004

(51) Int. Cl.⁷ .............................................. A61B 8/14
(52) U.S. Cl. ........................................................ 600/459
(58) Field of Search ................................ 600/437–472; 367/7, 103, 105, 130, 138; 29/25.35; 128/916

(56) References Cited

U.S. PATENT DOCUMENTS

| | | |
|---|---|---|
| 3,154,067 A | 10/1964 | Stenstrom et al. |
| 3,881,466 A | 5/1975 | Wilcox |
| 3,886,489 A | 5/1975 | Jones |
| 3,925,610 A * | 12/1975 | French et al. ............ 178/18.03 |
| 4,028,934 A | 6/1977 | Sollish |
| 4,059,010 A | 11/1977 | Sachs |
| 4,075,883 A | 2/1978 | Glover |
| 4,105,018 A | 8/1978 | Greenleaf et al. |
| 4,144,877 A * | 3/1979 | Frei et al. .................... 600/587 |
| 4,222,274 A | 9/1980 | Johnson |
| 4,250,894 A | 2/1981 | Frei et al. |
| 4,317,369 A | 3/1982 | Johnson |
| 4,515,165 A | 5/1985 | Carroll |
| 4,542,744 A | 9/1985 | Barnes et al. |
| 4,564,019 A | 1/1986 | Miwa |
| 4,662,222 A | 5/1987 | Johnson |
| 4,671,256 A | 6/1987 | Lemelson |
| 4,855,911 A | 8/1989 | Lele et al. |
| 4,858,124 A | 8/1989 | Lizzi et al. |
| 4,917,096 A | 4/1990 | Engelhart et al. |

(Continued)

FOREIGN PATENT DOCUMENTS

| | | | |
|---|---|---|---|
| AU | A-34432/95 | 2/1996 | |
| EP | 0 351 610 A2 | 1/1990 | |
| EP | 0 538 241 A2 | 4/1993 | |
| EP | 0 538 241 B1 | 4/1993 | |
| EP | 0 284 055 B1 | 9/1993 | |
| EP | 0 609 922 A2 | 8/1994 | |
| EP | 0 661 029 A1 | 7/1995 | |
| EP | 0 774 276 A2 | 5/1997 | |
| GB | 2040642 A * | 8/1980 | ............ H04R/7/00 |

OTHER PUBLICATIONS

Andre, et al. "A New Consideration of Diffraction Computed Tomography for Breast Imaging: Studies in Phantoms and Patients" *Acoustical Imaging*, J.P. Jones, Plenum Press, New York (1995), pp. 379–390.

Borup, et al. "Nonperturbative Diffraction Tomography Via Gauss–Newton Iteration Applied to the Scattering Integral Equation" *Ultrasonic Imaging*, Academic Press, Inc. (1992) vol. 14, pp. 69–85.

(Continued)

*Primary Examiner*—Ali Imam
(74) *Attorney, Agent, or Firm*—Townsend and Townsend and Crew LLP (57) ABSTRACT

An electret-based acoustic transducer array is provided and may be used in a system for examining tissue. The acoustic transducer array is formed with a substrate that has a multiple distinct cells formed therein. Within each of the distinct cells is positioned an acoustic transducing element formed of an electret material. A conductive membrane is formed over the distinct cells and may be flexible.

12 Claims, 5 Drawing Sheets

U.S. PATENT DOCUMENTS

| | | |
|---|---|---|
| 4,941,474 A | 7/1990 | Pratt, Jr. |
| 5,003,979 A | 4/1991 | Merickel et al. |
| 5,029,476 A | 7/1991 | Metala et al. |
| RE33,672 E | 8/1991 | Miwa |
| 5,143,069 A | 9/1992 | Kwon et al. |
| 5,158,071 A | 10/1992 | Umemura et al. |
| 5,179,455 A | 1/1993 | Garlick |
| 5,212,571 A | 5/1993 | Garlick et al. |
| 5,255,683 A | 10/1993 | Monaghan |
| 5,260,871 A | 11/1993 | Goldberg |
| 5,269,309 A | 12/1993 | Fort et al. |
| 5,280,788 A | 1/1994 | Janes et al. |
| 5,304,173 A | 4/1994 | Kittrell et al. |
| 5,318,028 A | 6/1994 | Mitchell et al. |
| 5,329,817 A | 7/1994 | Garlick et al. |
| 5,339,282 A | 8/1994 | Kuhn et al. |
| 5,349,954 A | 9/1994 | Tiemann et al. |
| 5,398,691 A | 3/1995 | Martin et al. |
| 5,413,108 A | 5/1995 | Alfano |
| 5,415,164 A | 5/1995 | Faupel |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,548,658 A | 8/1996 | Ring et al. |
| 5,553,618 A | 9/1996 | Suzuki et al. |
| 5,558,092 A | 9/1996 | Unger et al. |
| 5,573,497 A | 11/1996 | Chapelon |
| 5,582,173 A | 12/1996 | Li |
| 5,588,032 A | 12/1996 | Johnson et al. |
| 5,590,653 A | 1/1997 | Aida et al. |
| 5,596,992 A | 1/1997 | Haaland et al. |
| 5,606,971 A | 3/1997 | Sarvazyan |
| 5,620,479 A | 4/1997 | Diederich |
| 5,640,956 A | 6/1997 | Getzinger et al. |
| 5,643,179 A | 7/1997 | Fujimoto |
| 5,664,573 A | 9/1997 | Shmulewitz |
| 5,678,565 A | 10/1997 | Sarvazyan |
| 5,722,411 A | 3/1998 | Suzuki et al. |
| 5,743,863 A | 4/1998 | Chapelon |
| 5,762,066 A | 6/1998 | Law et al. |
| 5,766,129 A | 6/1998 | Mochizuki |
| 5,787,049 A * | 7/1998 | Bates .......................... 367/7 |
| 5,797,849 A | 8/1998 | Vesely et al. |
| 5,800,350 A | 9/1998 | Coppelson et al. |
| 5,810,731 A | 9/1998 | Sarvazyan et al. |
| 5,817,025 A | 10/1998 | Alekseev et al. |
| 5,833,614 A | 11/1998 | Dodd et al. |
| 5,833,634 A | 11/1998 | Laird et al. |
| 5,846,202 A | 12/1998 | Ramamurthy et al. |
| 5,865,167 A | 2/1999 | Godik |
| 5,865,743 A | 2/1999 | Godik |
| 5,891,619 A | 4/1999 | Zakim et al. |
| 6,002,958 A | 12/1999 | Godik |
| 6,005,916 A | 12/1999 | Johnson et al. |
| 6,078,677 A | 6/2000 | Dolleman et al. |
| 6,109,270 A | 8/2000 | Mah et al. |
| 6,117,080 A | 9/2000 | Schwartz |
| 6,135,960 A | 10/2000 | Holmberg |
| 6,190,334 B1 | 2/2001 | Lasky et al. |
| 6,425,869 B1 * | 7/2002 | Rafter et al. ............ 600/458 |
| 2002/0131551 A1 | 9/2002 | Johnson |

OTHER PUBLICATIONS

Chelfouh, et al. "Characterization of Urinary Calculi: In Vitro of 'Twinkling Artifact' Revealed by Color–Flow Sonography" *American Journal of Roentgenology* (1998) vol. 171, pp. 1055–1060.

Dean, Stanley R., "The Radon Transform and Some of Its Applications" *Krieger Publishing Company, Malabar, Florida* (1993).

Greenleaf, J.F. "Tissue Characterization with Ultrasound: vol. II: Results and Applications" *CRC Press, Inc.*, Boca Raton, Florida, pp. 95–122.

Greenleaf, J.F., et al. "Introduction to Computer Ultrasound Tomography" *Computed Aided Tomography and Ultrasonics in Medicine*, North–Holland, (1970); pp. 125–136.

Greenleaf, J.F., et al. "Mulitdimensional Visualization of Ultrasonic Images" *J. Acoust. Soc. Amer.* vol. 95 (2902), (1994).

Hebden, et al. "Acoustically Modulated Electrical Impedance Tomography" *Proceedings of the SPIE*, vol. 1231 (1990); pp. 7–14.

Jellins, J. "Breast Tissue Characterizations" *Tissue Characterization with Ultrasound*, vol. II, CRC Press, (1986); pp. 95–122.

Johnson, et al. "Modeling of Inverse Scattering and Other Tomographic Algorithms in Conjunction with Wide Bandwidth Acoustic Transducer Arrays for Towed or Autonomous Sub–bottom Imaging Systems" *Proceedings of Mastering the Oceans Through Technology*, Oceans Newport, Rhode Island, USA, (Oct. 26–29, 1992), pp. 294–299.

Johnson, et al. "Comparison of Inverse Scattering and Other Tomographic Imaging Algorithms Using Simulated and Tank Data for Modeling Subbottom Imaging Systems" IEEE Oceans '93 Symposium, Nov. 1993, vol. I, pp. 458–492 (1993).

Louvar, et al. "Correlation of Color Doppler Flow in the Prostate with Tissue Microvascularity" *Cancer*, (Jul. 1998) vol. 1:83(1); pp. 135–140.

Nelson, et al. "Interactive Acquisition, Analysis and Visualization of Sonographic Volume Data" *International Journal of Imaging Systems and Technology* (1997) vol. 8(26), pp. 26–37.

Sehgal, et al. "Visualization of Breast Calcification by Acoustic Resonance Imaging" *Radiology Supplement*, 84th Scientific Assembly and Annual Meeting, Nov. 29–Dec. 4, 1998 presented in McCormick Place, Chicago, Illinois (1998) vol. 209, listing: 1150.

Shi, et al. "Effects of Pressure Changes on Harmonic and Subharmonic Response of US Contrast Microbubbles" 84th Scientific Assembly and Annual Meeting, Nov. 29–Dec. 4, 1998 presented in McCormick Place, Chicago, Illinois (1998) vol. 209, listing: 1154.

Wiskin, et al. "Full Inverse Scattering vs. Born–like Approximation for Imaging in a Stratified Ocean" *Proc. of Engineering in harmony with the Ocean (Oceans '93)*, Victoria, British Columbia, Oct. 1993.

* cited by examiner

ELECTRET ACOUSTIC TRANSDUCER ARRAY FOR COMPUTERIZED ULTRASOUND RISK EVALUATION SYSTEM

STATEMENT AS TO RIGHTS TO INVENTIONS MADE UNDER FEDERALLY SPONSORED RESEARCH OR DEVELOPMENT

The Government has rights in this invention pursuant to U.S. Dept. of Energy Work for Others Agreement L-8420.

BACKGROUND OF THE INVENTION

The present invention relates generally to acoustic imaging systems. More particularly, the present invention relates to acoustic transducers for use in acoustic imaging systems.

There are a number of disadvantages associated with various imaging systems that are currently in use, particularly when used for medical applications. For example, a number of imaging techniques, such as x-ray imaging, mammography, and computed tomographic (CT) scans, use ionizing radiation that presents a risk of cell mutation when used medically. Also, CT scans and magnetic resonance imaging (MRI) techniques both involve procedures that are relatively expensive, a factor that by itself acts to some degree to limit their use. A significant disadvantage of methods such as mammography is that they rely on two-dimensional images that may disguise three-dimensional structure information that can be critical for diagnosis.

As an alternative to these imaging technologies, the medical community has looked to ultrasound for providing a safe, low-cost, high-resolution imaging tool. There are, however, significant limitations to conventional ultrasound, which may be used in A or B scanning modes. Such modes are distinguished by the fact that an A scan is purely one dimensional while a B scan produces a two-dimensional image. As a result, imaging applications tend to use ultrasonic B scanning. In such conventional ultrasound analysis, a small array of elements is moved by hand in contact with tissue under study. The array sends out waves that reflect from tissues back to the same array. This arrangement results in two major drawbacks. First, ultrasonic B scans do not provide information on the properties of the materials themselves; rather, they provide information only on the reflectivity of the boundaries between different types of materials. Second, the array is incapable of capturing radiation except that reflected back to the hand-held sensing array. Considerable information exists, however, in the transmitted waves, but this information is neither captured not used diagnostically in conventional ultrasonic B scans.

It is expected that improved diagnoses may result from systems that permit the collection of greater amounts of information. Factors that inhibit the development of such systems include limitations on the cost of appropriate acoustic transducers, such costs being influenced by needs for high sensitivity and small size. There is thus a general need for improved acoustic transducers that achieve such sensitivity and size, but which may be manufactured with simple processes that do not increase the cost prohibitively. Furthermore, there is a general need in the art for improved acoustic transducers that may readily be integrated into acoustic imaging systems, particularly as applied to medical applications.

BRIEF SUMMARY OF THE INVENTION

Embodiments of the invention thus provide an electret-based acoustic transducer array that may be used in a system for examining tissue. In one embodiment, the acoustic transducer array is formed with a substrate that has a plurality of distinct cells formed therein. Within each of the distinct cells is positioned an acoustic transducing element formed of an electret material. A conductive membrane is formed over the distinct cells and may be flexible. The distinct cells may be arranged linearly in a single dimension or may be provided in a two-dimensional arrangement. In some embodiments, a plurality of amplifiers may also be formed within the substrate, each such amplifier being connected with one of the acoustic transducing elements.

One or more such acoustic transducer arrays may be comprised by a sensor system that forms part of the system for examining tissue. In such an embodiment, a control system is additionally provided in communication with the sensor system and has a controller adapted to control the acoustic transducer arrays for insonifying the tissue and receiving scattered acoustic radiation from the tissue. The acoustic transducer arrays may be positioned such that the acoustic transducing elements are disposed to surround at least a portion of the tissue. For example, each acoustic transducer array may be positioned in one of a plurality of paddles, which may in certain embodiments include a pliable bladder for contacting the tissue.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and is enclosed in parentheses to denote one of multiple similar components. When reference is made to a reference numeral without specification to an existing sublabel, it is intended to refer to all such multiple similar components.

DETAILED DESCRIPTION OF THE INVENTION

Figure 1A:
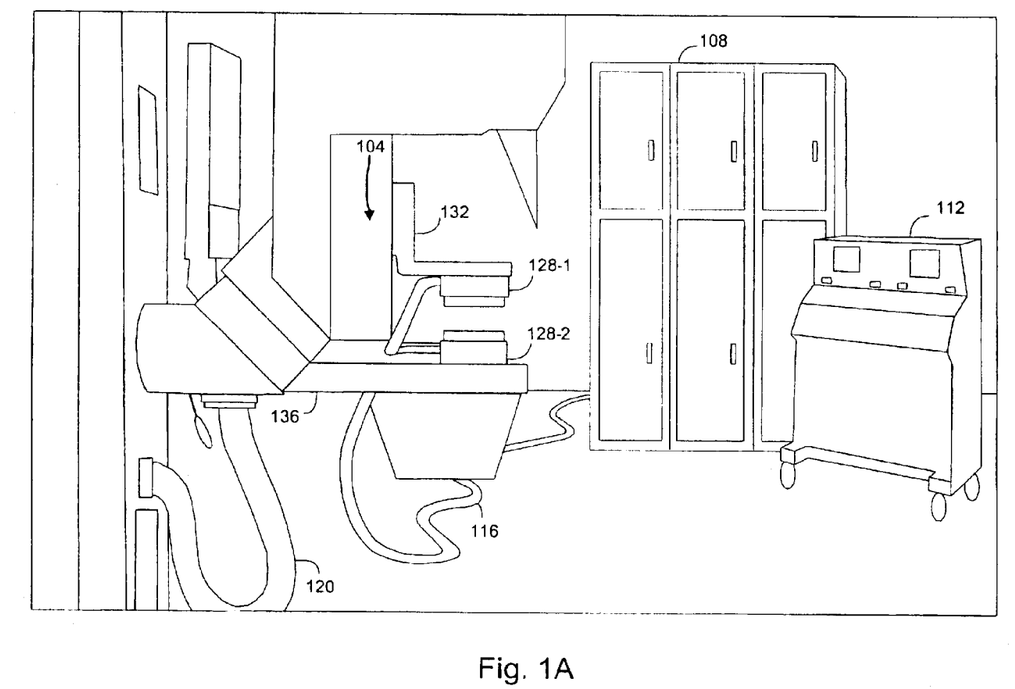
FIGS. 1A and 1B provide an overview of a system according to one embodiment of the invention, illustrated as a physical embodiment in FIG. 1A and illustrated schematically in FIG. 1B.
Figure 1B:
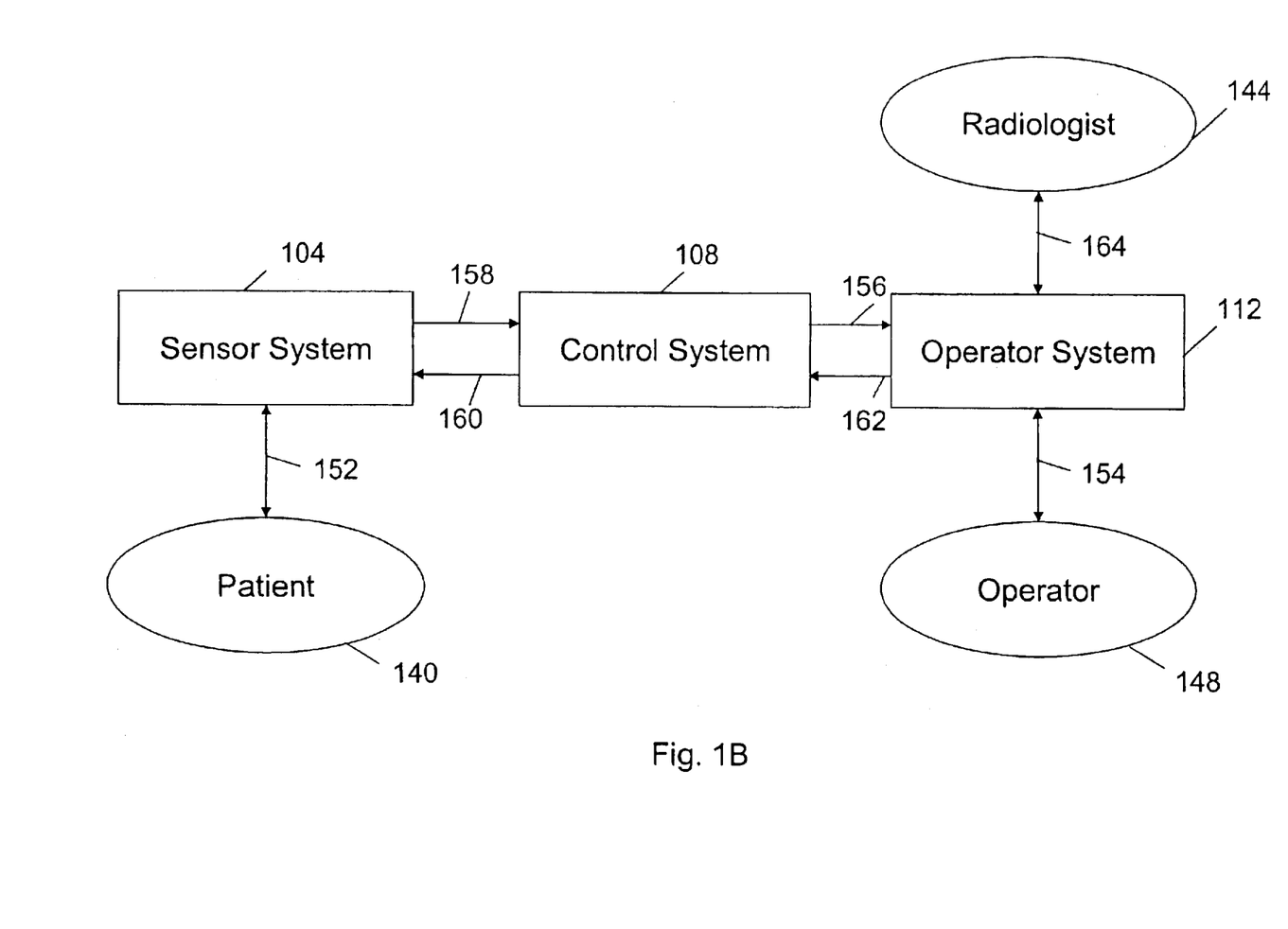

Embodiments of the invention are directed generally to acoustic transducer arrays that may be used in systems for examining objects under study, such as tissue. FIGS. 1A and 1B provide a general structural overview of such a system that may be configured according to an embodiment of the invention appropriate for medical applications, particularly for ultrasound imaging of a patient's breast. Additional aspects of such a system are described the following commonly assigned patents and patent applications, the entire disclosures of all of which are herein incorporated by reference for all purposes: U.S. Pat. No. 6,385,474 entitled "METHOD AND APPARATUS FOR HIGH-RESOLUTION DETECTION AND CHARACTERIZATION OF MEDICAL PATHOLOGIES," filed March 19, 1999 by John D. Rather et al., which is a nonprovisional of U.S. Prov. Pat. Appl. No. 60/078,788 entitled "HIGH RESOLUTION ULTRASOUND ANATOMICAL IMAGING SYSTEM," filed Mar. 20, 1998 by John D Rather; U.S. Pat. Appl. No. 10/323,354, entitled "COMPUTERIZED ULTRASOUND RISK EVALUATION SYSTEM," filed concurrently with the present application by Neb Duric et al. and U.S. patent application Ser. No. 10/323,467, entitled "DIAGNOSTIC ANALYSIS OF ULTRASOUND DATA," filed concurrently with the present application by David H. Chambers et al. While FIG. 1A shows the physical arrangement of the system components, FIG. 1B shows the logical interconnection of those components and how individuals interact with the system.

The system includes a sensor system 104, a control system 108, and an operator system 112. A connection 116 is provided for the transfer of information between the sensor system 104 and the control system 108 and a connection (not shown in FIG. 1A) is provided for the transfer of information between the control system 108 and the operator system 112. In some embodiments, such connections may comprise, for example, ethernet connections.

In the embodiment shown, the sensor system 104 includes a support 136, a source for power connections 120, and a sensor that includes a pair of paddles 128. The lower paddle 128-2 is fixed to the support 136, but the upper paddle 128-1 is configured to be moved with handle 132 to compress the patient's breast between the two paddles 128. Each of the paddles 128 comprises arrays of ultrasonic transmission and receiving elements (sometimes referred to herein generically as "transducing elements" or "transducers"). In one embodiment, 512 transmission elements and 512 receiving elements are provided in each paddle. A tomographic "view" is defined by data generated for transmission of acoustic radiation from a single transmission element and reception by a plurality of the receiving elements. A tomographic "slice" is defined by data generated for a plurality of views, i.e. derived from transmission of acoustic radiation from a plurality of transmission elements and reception by a plurality of receiving elements.

The control system 108 comprises hardware used to form and time ultrasonic transmission pulses. It further comprises circuitry that records the received ultrasonic waveforms. In one embodiment, the control system 108 is partitioned into a plurality of receiver cards that each comprise a plurality of channels. In one embodiment, 64 receiver cards are provided, each comprising 16 channels. A receive waveform from each channel is amplified and digitized with a high-dynamic-range analog-to-digital converter ("ADC"). After each transmission pulse, the waveform data are compressed and transferred to a local random-access memory ("RAM") capable of storing the waveform data for at least 100 tomographic slices. Such an architecture permits recordation of a tomographic slice in approximately 0.3 seconds so that the total acquisition time for a 100-slice breast scan is approximately 30 seconds.

Thus, in operation, the patient 140 has an interaction 152 with the sensor system 104 by being positioned so that the paddles 128 are contacting the patient's breast. The operator 148 has an interaction 154 with the operator system 112 to set up the operational parameters. In one embodiment, the operator system 112 is configured to provide a graphical user interface from which operational parameters such as mode selection and timing initiation may be established. The operator system 112 derives control information from the instructions provided by the operator 148, which is then transferred through interaction 162 to the control system 108.

Once the operation mode has been established, data acquisition by the sensor system 104 is initiated by a master timing pulse derived from a master timing oscillator comprised by the control system 108. Such a pulse is communicated to the sensor system through interaction 160. The sensor, shown as paddles 128 in the illustrated embodiment, insonifies the tissue volume and receives transmitted and reflected radiation. Transducing elements within the paddles 128 convert the received acoustic information into electrical signals that are communicated back to the control system 108 through interaction 158. The control system 108 performs an analysis of the electrical signals to derive image information that is returned to the operator system 112 through interaction 156. A professional evaluator 144, such as a radiologist, may then interact directly with the operator system 112 to view the rendered data. In alternative embodiments, selected views of the rendered data may be printed or stored for later viewing and analysis by the evaluator 144.

According to embodiments of the invention, the transducing elements comprised by the sensor system 104 comprise electric material and may be configured in the form of an acoustic transducer array. Electret materials are of a general class of materials that may be processed so that they maintain a permanent electric field set in a manner analogous to permanently magnetizing a magnetic material. For example, certain electrets may be made of organic compounds by cooling from a liquid or soft state to the solid state in the presence of an electric field or through polymerization in the presence of an electric field. Typical materials that may be used to make electrets include beeswax and polymers such as polyvinylidene fluoride. Such electrets are useful as transducing elements since their mechanical impedance is well matched to the impedance of living tissue. In some instances, the consistency of an electret may be changed by using different substances or combinations of substances. Matching impedance of the transducing elements to the tissue has the advantage of higher sensitivity and better signal-to-noise ratio.

The use of such electret materials as transducing elements derives from the fact that they generally have piezoelectric properties, i.e. deformation of the electret material results in a change in electric field. The ability to respond to deformations such as may be provided by acoustic waves makes the material suitable as a receiving element R. Alternatively, the electret material may be used as a transmission element T by imposing an additional periodic electric field to produce acoustic waves from the resulting periodic deformation of the material.

Figure 2:
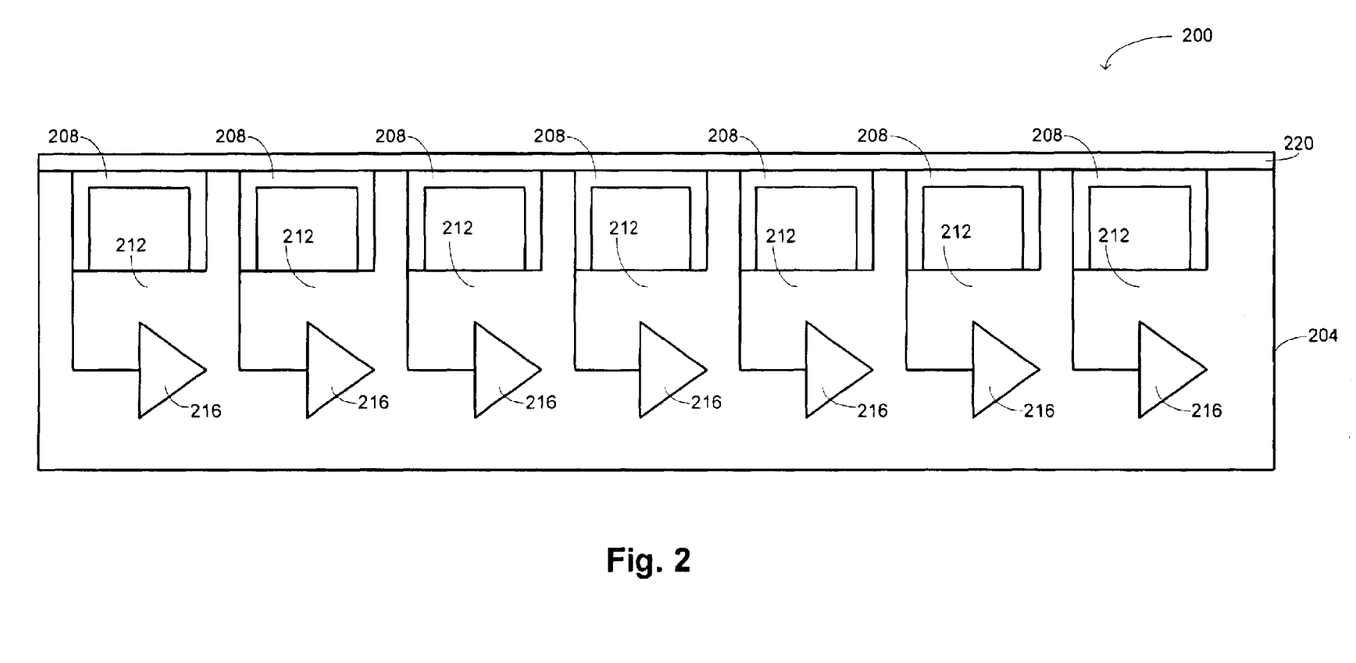
FIG. 2 provides a schematic illustration of an electret acoustic transducer array in accordance with an embodiment of the invention.

One embodiment in which the acoustic transducing elements are configured as an array is illustrated in FIG. 2, which schematically shows an arrangement of such elements formed on a common substrate. The use of a common substrate provides a number of advantages, including the ability to produce the array with a small size and the ability to use simple manufacturing techniques, such as micromachining techniques, to produce the array. For example, in FIG. 2, the transducer array is denoted generally as 200 and includes a plurality of distinct cells 208 formed within a substrate 204. The array of cells may take different configurations in different embodiments. For example, it may be configured linearly in a single dimension or may be configured as a two-dimensional array. Such a two-dimensional array may be rectangular, circular, or have a different shape depending on the specific desired application. Within each cell 208, an acoustic transducing element 212 formed of an electret material is provided. A low-mass conductive layer 220 is applied over the cells 208. In some embodiments, the conductive layer 220 is flexible to permit transmission of acoustic waves into the cells 208.

There are various ways in which such an array may be manufactured, including using micromachining techniques. For example, the common substrate may comprise a silicon substrate within which the cells 208 are formed using a combination of patterning and etching. The patterning, such as produced by optical exposure of photoresist through a mask, is used to define the configuration of the array, and a suitable anisotropic etching technique, such as wet anisotropic etching, plasma etching, reactive-ion etching ("RIE"), or deep reactive-ion etching ("DRIE"), is used to produce the cells 208. The electret material is deposited within the individual cells 208 using any suitable deposition technique, which includes epitaxy, oxidation, sputtering, evaporation, various forms of chemical-vapor deposition, spin-on methods, sol-gel methods, anodic bonding, electroplating, and fusion bonding.

In embodiments where the transducing elements 212 are configured as receivers, each of the cells 208 may be connected with a preamplifier 216 integrated within the substrate 204. After the electret material converts received acoustic signals into electrical signals, such a preamplifier 216 is used to boost the electrical signals and allow sufficient power to drive signal cables. In other embodiments, the transducing elements 212 may be configured as transmitting elements. It is advantageous in various applications for some of the transducing elements 212 to be configured as receivers and for other of the transducing elements to be configured as transmitting elements.

The transducer array 200 may be incorporated into a variety of configurations. One embodiment, shown explicitly in FIGS. 3A–3C, uses a pair of acoustic paddles 128. Such a paddle arrangement has the advantage when used with breast imaging of leaving a portion of the breast exposed to perform biopsy extractions. Such biopsy extractions may be performed in response to data previously acquired, or the imaging system may instead be used to provide real-time guidance for performing a very accurate biopsy. In addition, specific embodiments use a geometry that is particularly effective at insonifying the axilla region and tissues near the chest wall. Such regions are important sites for breast cancer detection, but are not as well examined by using, for example, a circular array geometry.

Figure 3A:
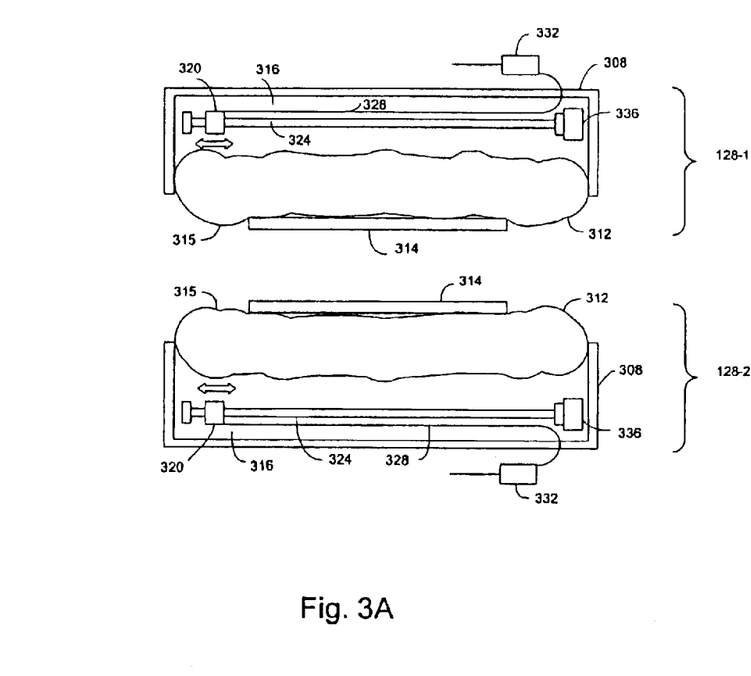
FIG. 3A provides a cross-sectional view of a paddle arrangement used for insonification of tissue.

FIG. 3A shows a cross-sectional view of both the upper 128-1 and lower paddles 128-2 in one embodiment. Each of the acoustic paddles 128 comprises an enclosure 308 and a pliable coupling bladder 312. The enclosure 308 comprises an acoustic transmission medium 316. In one embodiment, the enclosure 308 further comprises an acoustic-energy absorbing material to reduce unwanted reflections when the sensor system is in operation.

The pliable coupling bladder 312 is filled with a medium that is acoustically matched to the transmission medium 316. In operation, the exterior portion of the coupling bladder 312, i.e. that portion that is to be in contact with a patient's tissue, is coated with a coupling gel. The quality of data generated may be adversely affected by the presence of bubbles when the paddle is placed in contact with the tissue. The pliability of the coupling bladder 312 thus provides an adaptable interface for improving patient contact and reducing trapped air bubbles. In some instances, only a portion of the coupling bladder 312 is pliable, depending on characteristics of the tissue to be studied, particularly the firmness of the tissue to be studied. Patient scanning follows an approximately inverse law of firmness in relation to the surface being scanned. For example, imaging of a soft organ such as the breast benefits from a firmer flat surface to squeeze out bubbles during mild initial compression. Conversely, imaging of firm and/or irregular contours such as a joint surface benefits from greater pliability. A coupling bladder 312 that includes both firm portions 314 and pliable portions 315 may thus effectively accommodate specific tissue configurations. For example, the coupling bladder 312 for use in breast examination may be pliable on the portion of the paddle 128 extending into the firmer tissues of the axilla, with the remainder of the paddle 128 being flat and firm to better squeeze out air bubbles in contact with the compliant breast tissue. The resultant ability to facilitate insonification of the axilla region is beneficial because it permits acoustic coupling of regions that are traditionally difficult to reach.

In the illustrated embodiment, a transducer array 320 configured with a plurality of electret transducing elements formed in cells of a common substrate is included within the transmission medium 316 of each paddle. Depending in part on the specific application, the array 320 may be configured in a one- or two-dimensional pattern. For example, in a particular embodiment, the array 320 is configured as a monolithic linear assembly that extends orthogonally to the cross section shown in FIG. 3A. In that embodiment, it is further configured as part of a carriage subsystem for moving the array 320 in an orthogonal direction, i.e. left-right in FIG. 3A. Such movement permits the array 320 to scan through the tissue to be examined. Thus, in addition to the electret-transducer array 320, the carriage subsystem comprises translation elements, such as a lead screw arrangement 324 and mount 336. Other translation mechanisms, such as use of a recirculating ball, will be known to those of skill in the art and may be substituted for the illustrated arrangement.

Figure 3B:
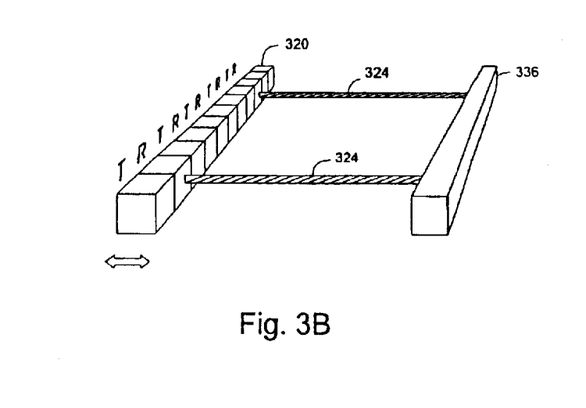
FIG. 3B provides a perspective view of acoustic arrays that may be used within the paddle arrangement.

A detail of the electret-transducer array 320 and translation mechanism is shown in FIG. 3B for a specific embodiment. In that embodiment, each array 320 uses alternating transmitting and receiver elements formed within the common substrate. Generally, the spacing ("pitch") between the receiver elements R is set substantially equal to one half wavelength for the average speed of sound in the appropriate tissue in order to satisfy the spatial Nyquist criterion. For example, where the tissue to be imaged comprises breast tissue, the pitch between receiver elements for a center frequency of 2 MHz is approximately 0.385 mm. The transmitting elements T are generally placed at the same pitch as the receiver elements R, and is readily accomplished by virtue of the alternating linear arrangement.

The translation mechanisms of the two acoustic arrays in the upper 128-1 and lower paddles 128-2 are configured so that the arrays are positioned substantially opposite each other in the same acoustic plane with the opposing elements facing each other. Thus, in a specific embodiment, each of the transmitting elements T sends a pulse that insonifies the intermediate tissue. The acoustic waveform scattered from the tissue is received by the receiving elements R.

Figure 3C:
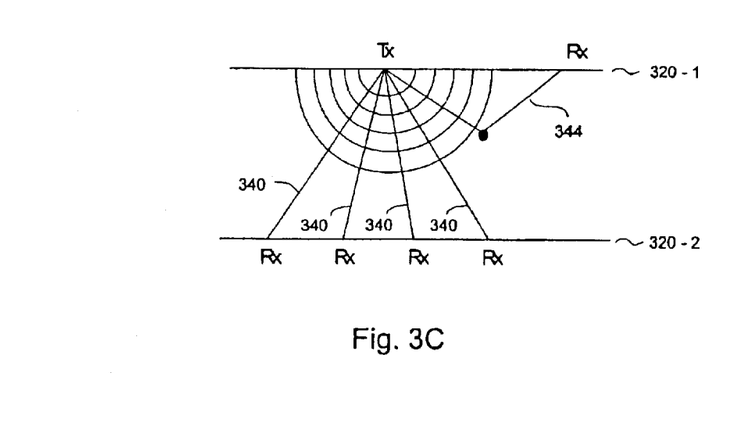
FIG. 3C provides a schematic illustration of how waves are propagated within the paddle arrangement between transmission and receiving elements.

This is shown schematically in FIG. 3C, in which a single transmit pulse $T_x$ results in a plurality of received signals $R_x$. Some of the received signals, denoted by rays 340 in FIG. 3C, correspond to transmission through the tissue so that they are received by a receiving element R on a different acoustic array 128 than the transmission element T. Other received signals, such as the one denoted by ray 344, correspond instead to reflection from the tissue so that they are received by a receiving element R on the same acoustic array 128 as the transmission element T. For the physical arrangement shown, cylindrically or spherically shaped wave fronts emanating from each transmitting element T provide sufficient angular diversity to achieve suitable resolution for tomographic reconstruction.

In one mode of operation, the beam pattern produced for each slice is wide in an image plane but is narrow in a thickness plane. After a slice has been taken, both acoustic arrays 128 are moved a distance through the thickness plane and the cycle is repeated. While such a method of operation is suitable for normal tomographic scans, the system is also amenable to alternative scanning techniques. For example, for B scans, a group of transmission elements T may be activated simultaneously to form a plane wave across the tissue rather than forming a series of acoustic pulses.

Figure 4:
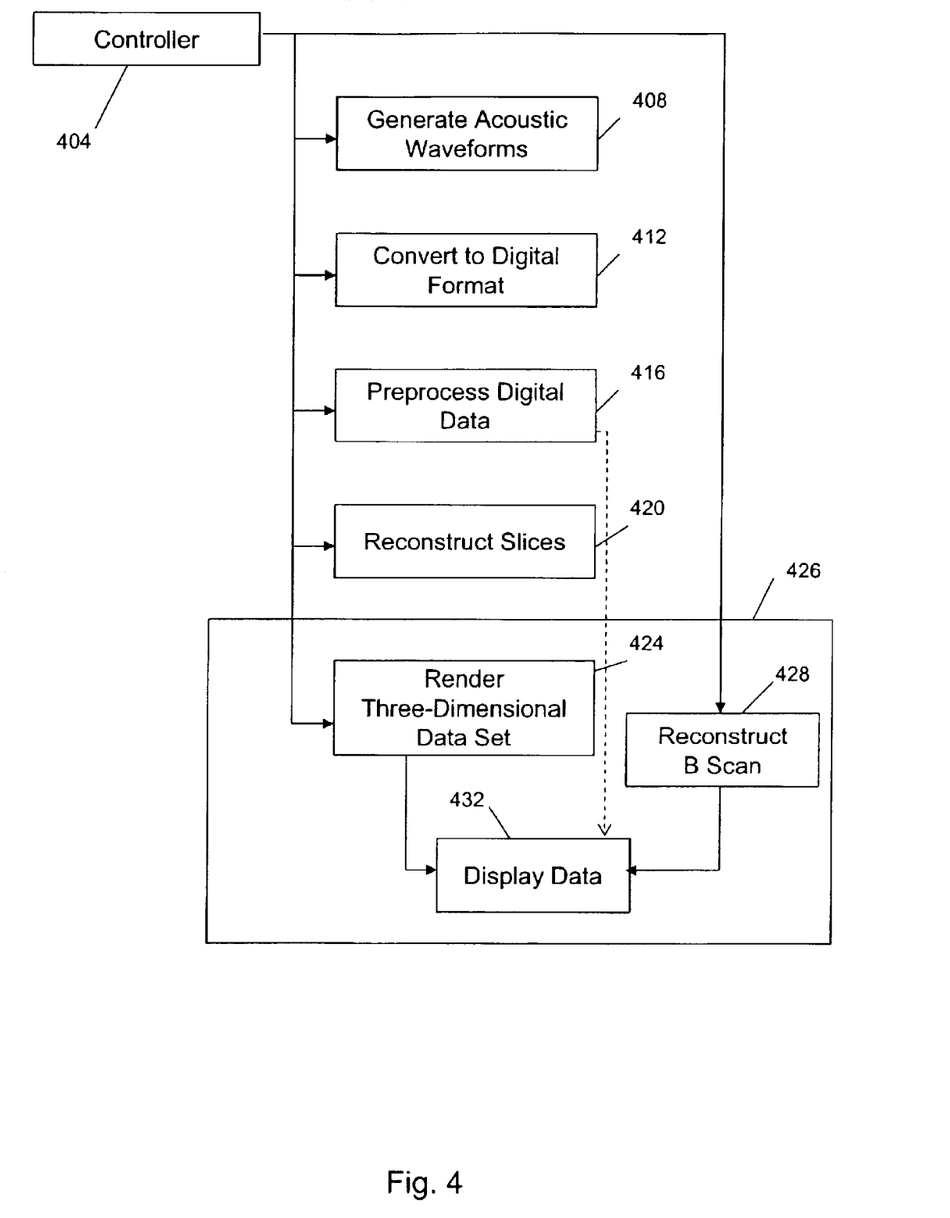
FIG. 4 provides a flow diagram providing an overview of the functional hierarchy used in an embodiment.

FIG. 4 provides a overview of the functional hierarchy of the system and indicates eight primary functions performed by the system. These functions may be implemented with any suitable computational device, such as a computer. At block 404, a controller function is provided for the system. The controller function comprises coordinating the generation of acoustic waveforms at block 408, conversion of the waveforms to digital format at block 412, preprocessing the digital data at block 416, reconstructing B-scan images at block 428, reconstructing two-dimensional slices at block 420, rendering three-dimensional data sets at block 424, and displaying data and images at block 432. In each instance, the controller function comprises defining setup conditions for each of the other functions and determining when the function is complete.

The generation of acoustic waveforms at block 408 comprises: (1) positioning acoustic transducers for each tomographic slice; (2) generating the acoustic pulses to insonify the tissue; (3) capturing waveforms transmitted through and reflected from the tissue; and (4) using acoustic pulse timing signals to control the conversion function at block 412. The acoustic transducers are positioned by first moving them to a known home position prior to a scan cycle. The number of tomographic slices to be generated and the spacing between the slices is then received from the controller function 404. These acoustic pulses are generated by receiving transmit setup information form the controller function 404, the transmit setup information including the number and location of the transmission elements, the ganging of the transmission elements, the wave shape of the transmit pulse, and the transmit timing. Acoustic pulses are thus generated according to the setup parameters.

Once the transmitted and reflected waveforms are captured, they are processed by the conversion function at block 412. Such conversion into digital format comprises receiving both conversion setup information from the controller function 404 and receiving waveforms and timing signals from the generation function 408. In one embodiment, the minimum sampling is at least three times the highest frequency of interest, equivalent to 1.5 times the Nyquist criterion. The waveforms are converted to digital format under control of the timing signals and the digitized data are sent to the preprocessing function at block 416.

At block 416, the digitized data are preprocessed. This preprocessing comprises receiving setup information from the controller function 404 and receiving timing information from the conversion function 412. Regardless of the type of preprocessing called for by the controller function 404, the preprocessing function 416 reduces the amount of data collected by limiting the bandwidth of the data and by limiting the number of data samples. These windowed data are saved for further processing. In one embodiment, depending on the setup parameters received from the control function, preprocessing comprises determining the time of arrival and the amplitude of the direct coupling pulse; the direct coupling pulse is then removed and the remainder of the time series of data is retained, from which the complex phase and amplitude are determined for the remaining data. In certain embodiments, preprocessing further comprises sending data-quality images to the display function so that the operator 148 can assess the quality of the data being collected.

At block 420, two-dimensional tomographic slices are reconstructed. In embodiments having a plurality of sensor systems 104, each reconstruction may be coordinated by a central control system 108 rather than requiring a reconstruction system to be associated with each sensor system. Reconstructing such slices comprises receiving setup parameters and a signal to begin reconstruction from the controller function 404. Preprocessed data are received from the preprocessing function 416 and may perform any of a variety of reconstructions described in detail below. Such reconstruction algorithms include, without limitation, full-aperture tomography ("FAT") algorithms, quantitative full-aperture tomography ("QFAT") algorithms, diffraction tomography algorithms, and full-wave reconstruction algorithms. In some embodiments, a plurality of reconstruction algorithms are executed on the same data set to provide additional diagnostic information.

The two-dimensional reconstructed slices are assembled into a three-dimensional data set. In one embodiment, each element of the three-dimensional data set contains values for at least one physical quantity, such as sound speed, attenuation, density, compressibility, reflectivity, absorption, and/or acoustic impedance changes from each of the reconstructions. A three-dimensional data set is thus rendered at block 424 upon receipt of setup information from the controller function 404, with a signal to display the rendered data. In one embodiment, the rendering is capable of providing three orthogonal views of arbitrary orientation and position. In another embodiment, the rendering is capable of superimposing data derived from a plurality of reconstruction techniques. Such a plurality of reconstruction techniques permit production of isosurface or semitransparent volume rendering.

At block 428, B-scan images are reconstructed. Such reconstruction comprises receiving setup information from the control system and receiving data and timing signals from the preprocessing function 416.

At block 432, data are displayed in the form of images. Rendered images and B-scan images are received from the rendering function 424 and from the B-scan reconstruction function and displayed for the operator 148. In certain embodiments, data-quality images derived from the preprocessing function 416 are also displayed so that the operator 148 may assess the quality of the data being collected.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A system for examining tissue, the system comprising:
   a sensor system having at least one acoustic transducer array, each such acoustic transducer array comprising:
   a substrate having a plurality of distinct cells formed therein;
   a plurality of acoustic transducing elements, each such acoustic transducing element being formed of an electret material and positioned within one of the distinct cells; and
   a flexible conductive membrane formed over the distinct cells; and
   a control system in communication with the sensor system, the control system comprising a controller adapted to control the at least one acoustic transducer array for insonifying the tissue and receiving scattered acoustic radiation from the tissue, wherein the received scattered acoustic radiation includes a mix of reflected and transmitted acoustic waves.

2. The system recited in claim 1 wherein the at least one acoustic transducer array comprises a plurality of acoustic transducer arrays positioned such that the plurality of acoustic transducing elements are disposed to surround at least a portion of the tissue.

3. The system recited in claim 2 wherein the sensor system further comprises a plurality of paddles, each such paddle including at least one of the plurality of acoustic transducer arrays.

4. The system recited in claim 3 wherein each such paddle further includes a pliable bladder for contacting the tissue.

5. The system recited in claim 1 wherein each such acoustic transducer array further comprises a plurality of amplifiers formed within the substrate, each such amplifier being connected with one of the acoustic transducing elements.

6. The system recited in claim 1 further comprising a translation element configured to move the at least one acoustic transducer array to scan a portion of the tissue.

7. A method for examining tissue, the method comprising:
   insonifying the tissue;
   receiving scattered acoustic radiation from the tissue with an acoustic transducer array having a plurality of acoustic transducing elements formed of an electret material and positioned within distinct cells of a substrate, wherein the acoustic transducer array is disposed to surround at least a portion of the tissue, whereby the received scattered acoustic radiation includes a mix of reflected and transmitted acoustic waves; and
   generating a representation of the portion of the tissue from the received scattered acoustic radiation.

8. The method recited in claim 7 wherein the acoustic transducer array comprises a plurality of acoustic transducer arrays.

9. The method recited in claim 7 wherein receiving scattered acoustic radiation comprises moving the acoustic transducer array.

10. A system for examining tissue, the system comprising:
    means for insonifying the tissue;
    means for receiving scattered acoustic radiation from the tissue including an acoustic transducer array having a plurality of electret transducing means for converting the scattered acoustic radiation into electrical signals, each such electret transducing means being formed within distinct cells of a substrate, wherein the means for receiving scattered acoustic radiation is disposed to surround at least a portion of the tissue, whereby the received scattered acoustic radiation includes a mix of reflected and transmitted acoustic waves; and
    means for generating a representation of the portion of the tissue from the electrical signals.

11. The system recited in claim 10 wherein the means for receiving scattered acoustic radiation from the tissue further includes means for amplifying the electrical signals formed within the substrate.

12. The system recited in claim 10 wherein the acoustic transducer array is moveable.

* * * * *